(12) United States Patent
Volpicelli et al.

(10) Patent No.: US 8,927,740 B2
(45) Date of Patent: Jan. 6, 2015

(54) ASYMMETRIC REDUCTION PROCESS

(75) Inventors: Raffaella Volpicelli, Vicenza (IT); Mauro Andretto, Noventa Vicentina (IT); Livius Cotarca, Cervignano del Friuli (IT); Antonio Nardi, Gambellara (IT); Massimo Verzini, Caldiero (IT)

(73) Assignee: Zach System S.P.A., Bresso (Milan) (IT)

( * ) Notice: Subject to any disclaimer, the term of this patent is extended or adjusted under 35 U.S.C. 154(b) by 0 days.

(21) Appl. No.: 14/003,385

(22) PCT Filed: Mar. 8, 2012

(86) PCT No.: PCT/EP2012/054023
§ 371 (c)(1),
(2), (4) Date: Sep. 5, 2013

(87) PCT Pub. No.: WO2012/120086
PCT Pub. Date: Sep. 13, 2012

(65) Prior Publication Data
US 2013/0338377 A1    Dec. 19, 2013

(30) Foreign Application Priority Data

Mar. 10, 2011  (IT) .............................. MI2011A0365
Jun. 8, 2011   (IT) .............................. MI2011A1028

(51) Int. Cl.
*C07D 495/04*    (2006.01)
(52) U.S. Cl.
CPC .................................... *C07D 495/04* (2013.01)
USPC ......................................................... 549/23
(58) Field of Classification Search
CPC ...................................................... C07D 495/04
USPC ......................................................... 549/23
See application file for complete search history.

(56) References Cited

U.S. PATENT DOCUMENTS 5,580,764 A     12/1996  Holt et al.
2007/0225528 A1*  9/2007  Noyori et al. ................. 568/700

FOREIGN PATENT DOCUMENTS

CN    101735209      6/2010
WO    2006/070387    7/2006

OTHER PUBLICATIONS

Noyori et al. (J. Org. Chem. 2001, 66(24); 7931-7944).*
Blacklock et al. (J. Org. Chem. 1993, 58 (7); 1672-1679).*
Mathre D J, et al., A Practical Process for the Preparation . . . , J. Org. Chem, vol. 58, pp. 2880-2888, 1993.
Aidan M. Hayes, et al., A Class of Ruthenium(II) Catalyst . . . , J. Am. Chem. Soc., vol. 127, pp. 7318-7319, 2005.
International Search Report issued in counterpart PCT/EP2012/054023.
Written Opinion of the ISA issued in counterpart PCT/EP2012/054023.

* cited by examiner

*Primary Examiner* — Kristin Vajda
*Assistant Examiner* — Valerie Rodriguez-Garcia
(74) *Attorney, Agent, or Firm* — Silvia Salvadori, P.C.

(57) ABSTRACT

The present invention relates to a stereoselective reduction procedure to obtain, by means of catalytic asymmetric hydrogenation by hydrogen transfer, a compound of formula (I) in which X is S or $SO_2$ and $R_4$ is hydrogen or an $SO_2NH_2$ group, from the corresponding ketone precursor, said compound of formula (I) being useful as an intermediate in the preparation of dorzolamide or of the hydrochloride salt thereof.

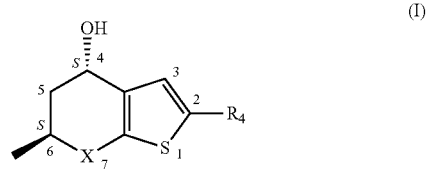

(I)

15 Claims, No Drawings

ASYMMETRIC REDUCTION PROCESS

The present invention relates to an asymmetric reduction process for the preparation of a compound of formula (I)

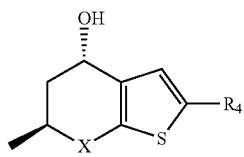

(I)

in which X is S or $SO_2$ and $R_4$ is hydrogen or $SO_2NH_2$, said compound being useful as an intermediate in the preparation of dorzolamide, whose hydrochloride salt is the active ingredient contained, for example, in the drug Trusopt™, which is suitable for the treatment of ocular hypertension, which causes glaucoma.

The invention also relates to the preparation of dorzolamide and of the hydrochloride salt thereof by means of this intermediate.

European patent EP 296879 describes compounds which are active as carbonic anhydrase inhibitors, including the compound (4S,6S)-4-(N-ethylamino)-5,6-dihydro-6-methyl-4H-thieno[2,3-b]thiopyran-2-sulfonamide-7,7-dioxide, whose International Non-proprietary Name (INN) is dorzolamide, of formula:

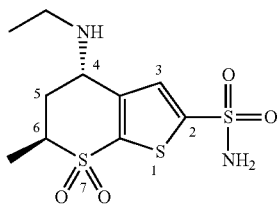 [SMILES: CCN[C@H]1C[C@H](C)S(=O)(=O)c2sc(S(N)(=O)=O)cc21]

In the patent EP 296879, enantiomerically pure dorzolamide is obtained by means of intermediates which are enantiomeric mixtures, and use of a chromatography column and a chiral resolvent agent in the final phases of synthesis, with a consequent significant reduction in the reaction yields.

Other known processes for obtaining dorzolamide use more convenient enantioselective methods, which use intermediates already having a chiral structure, thus allowing to obtain the final product in the desired form in a more advantageous manner.

Among these chiral intermediates, the compound of formula (I), in which X is $SO_2$ and $R_4$ is hydrogen, namely the compound (4S,6S)4-hydroxy-6-methyl-5,6-dihydro-4H-thieno[2,3-b]thiopyran-7,7-dioxide (hereinafter also referred to as trans-hydroxy sulfone), is commonly used as a key intermediate in many synthetic schemes known in the art.

The preparation of trans-hydroxy sulfone or of the compound of formula (I), in which X is S and $R_4$ is hydrogen (hereinafter also referred to as trans-hydroxy sulfide), which also contains two chiral centres of S,S configuration in positions $C_4$ and $C_6$ of the structure, has proven to be particularly challenging for a person skilled in the art. For example, the use of common non-chiral reducing agents, such as $NaBH_4$, $LiAlH_4$ and $ZnBH_4$, on the ketone precursor of formula (II)

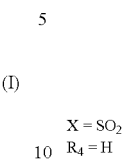

(II)

$X = SO_2$
$R_4 = H$ which has a methyl group in position $C_6$ with S configuration, leads to the obtainment of cis-hydroxy sulfone, in which the two chiral centers in positions $C_4$ and $C_6$ of the structure have R,S configuration respectively, with high diastereoisomeric excess (de>90).

Many attempts have been made to prepare trans-hydroxy sulfone, in which the two chiral centers in positions $C_4$ and $C_6$ of the structure have S,S configuration respectively, with a suitable degree of purity.

A further example, namely the process suggested by Blacklock et al., J. Org. Chem., 1993, 58 1672-1679, which comprises the reduction of the ketone precursor of formula (II) of the compound of formula (I), wherein X is S and $R_4$ is hydrogen, does not provide the corresponding compound of formula (I) with the hydroxyl in $C_4$ in the desired S configuration, but instead predominantly gives the diastereoisomer having the hydroxyl in R configuration, and further steps are needed to obtain the desired trans-hydroxy sulfide, in accordance with Scheme 1:

Scheme 1

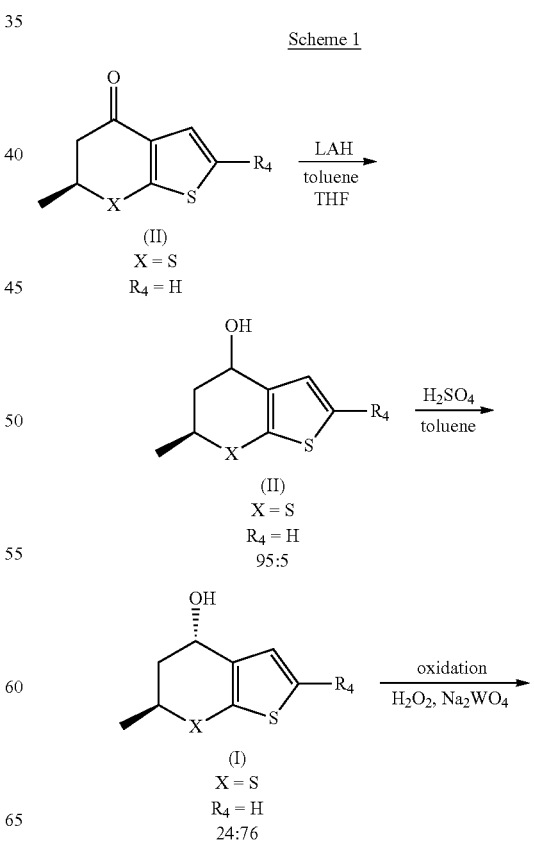

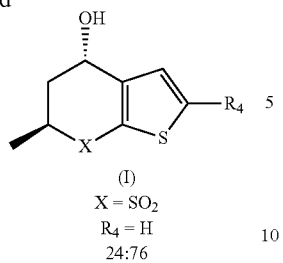

(I)
X = SO$_2$
R$_4$ = H
24:76

It is clear from Scheme 1 that, once the chiral centre S has been installed in position C$_6$ of the ketone precursor, the reduction of the ketone to give the trans-hydroxy sulfide is inhibited by the steric hindrance of the methyl group, so that hydroxy sulfide in which the hydroxyl has the R configuration is predominantly obtained, and a further step is necessary to obtain the desired inversion of configuration in position C$_4$ and to obtain trans-hydroxy sulfide, namely the compound of formula (I) wherein X is S and R$_4$ is hydrogen, which is then oxidised to obtain trans-hydroxy sulfone, namely the compound of formula (I) wherein X is SO$_2$ and R$_4$ is hydrogen.

Also in U.S. Pat. No. 5,157,129, the enantioselective reduction of the ketone precursor from a borane derivative as a reducing agent and oxazaborolidine as a catalyst results predominantly in chiral hydroxy sulfone of cis configuration, with a high degree of purity. The cis hydroxyl group is converted into the corresponding desired trans ethylamino group by means of conversion of the hydroxyl into the corresponding tosylate and the subsequent nucleophilic substitution with the ethylamino group.

U.S. Pat. No. 5,319,772 shows another method for converting the hydroxyl group present in cis-hydroxy sulfone into the corresponding ethylamino group in a complete diastereoselective manner, for example by means of introduction of an azide in position C$_4$, using phosphoryl azide to obtain the desired inversion of configuration.

EP 1813618 describes another method for obtaining inversion of configuration of cis-hydroxy sulfone in the corresponding ethylamine having opposite configuration, by reacting the hydroxylic group in position C$_4$ of the cis-hydroxy sulfone with a sulfamide group, in the presence of a phosphine and of an alkyl-azodicarboxylate compound and therefore by deprotecting the corresponding sulfamide derivative, giving rise to the trans-amine derivative.

Jones et al., J. Org. Chem. 1991, 56, 763-769 discovered a way of achieving the enantioselective reduction of a desmethyl analogue of the ketone precursor of formula (II), wherein X is SO$_2$ and R$_4$ is hydrogen, to give the corresponding hydroxy sulfone, using yeasts (Saccharomyces cerevisiae) with reaction yields of 89:11 in favour of the hydroxyl with S configuration in position C$_4$, as described in Scheme 2:

Scheme 2

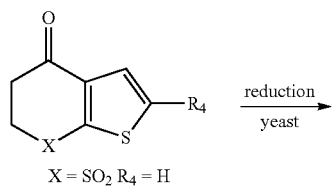

X = SO$_2$ R$_4$ = H

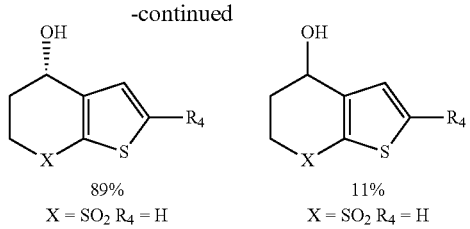

89%
X = SO$_2$ R$_4$ = H

11%
X = SO$_2$ R$_4$ = H

According to EP 658211, when a series of bread and beer yeasts were tested to reduce the ketone precursor of formula (II) wherein X is SO$_2$, the undesired cis-hydroxy sulfone was instead obtained predominantly.

Furthermore, EP 658211 describes the selective asymmetric conversion of the ketone precursor of formula (II), wherein X is SO$_2$ and R$_4$ is hydrogen into trans-hydroxy sulfone using an enzyme-type reduction system provided by whole or broken cells of suitable microorganisms. The success of stereoselective conversion induced by microorganisms or enzymes is also described in U.S. Pat. No. 5,474,919, U.S. Pat. No. 5,760,249 and in CN102154231A.

In the prior art therefore, selective reduction to trans-hydroxy sulfone has been carried out exclusively with the aid of reductive bioconversion methods, wherein selective reduction leads to a process, which allows to obtain a product with high diastereoisomeric excess.

The bioconversion processes induced by microorganisms described above are carried out in highly diluted solutions (for example from 1 to 3%) and require long and laborious work-up, particularly for the separation of the biomasses. These factors contribute to a reduction in the productivity and efficiency of the process, thus increasing costs.

Another disadvantage associated with bioconversion processes is linked to the fact that the cells in the bioreactors are subjected to stress produced by the reaction itself, by the raw materials introduced and by the impurities present, which, in combination with the sudden pH and temperature changes occurring in the bioreactors, contributes to a reduction in efficiency and economic value of this technology.

Last but not least, it is noted that bioconversions carried out with the aid of enzymes require the presence of "cofactors", which are generally very costly, thus requiring the implementation of recycle flows to make the processes competitive.

The several undesired effects described above associated with the bioconversion system with the aid of microorganisms have been overcome by our inventors, who have found a way of preparing trans-hydroxy sulfone or trans-hydroxy sulfide in a more efficient and economically advantageous manner, avoiding the step of bioreduction of the ketone precursor and utilising the technology described by Noyori et al. in J. Am. Chem. Soc., 1996, 118, 2521-2522; J. Am. Chem. Soc., 1995, 117, 7562-7563; Org. Biomol. Chem., 2006, 4, 393-406; J. Am. Chem. Soc., 1997, 119, 8738-8739; J. Org. Chem., 1999, 64, 2186-2187; Wills et al., J. Am. Chem. Soc., 2005, 127, 7318; and Wills et al., J. Org. Chem., 2005, 70, 3188 for reduction of the ketosulfone and ketosulfide compounds.

However, a person skilled in the art would be expecting to obtain, predominantly, the cis-diastereoisomer of a compound of formula (I) in which the hydroxyl has an R configuration in position C$_4$, subjecting a compound of formula (II)

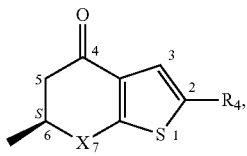

(II)

wherein X is S or $SO_2$ and $R_4$ is hydrogen or $SO_2NH_2$, to the asymmetric catalytic reduction taught by Noyori, taking into account the fact that, as already mentioned above, the reduction of the ketone group in position $C_4$ to give a trans-derivative is inhibited by the steric hindrance of the methyl group in position $C_6$.

Our inventors have surprisingly found that, by applying the aforementioned technique of catalytic asymmetric reduction to a compound of formula (II), not only when $R_4$ is hydrogen, but also when $R_4$ is $SO_2NH_2$, the corresponding compound of formula (I), as defined above, is obtained, wherein the hydroxyl in position $C_4$ has S configuration, and therefore it is not necessary either to carry out further steps to obtain inversion of configuration in said position, or to use bio catalytic techniques, the disadvantages of which have already been broadly discussed above.

In addition, the method object of the present invention is advantageous for practical scale-up and for industrial production and does not require the use of special, dedicated equipment, such as a hydrogenator for pressure catalytic hydrogenation or specific bioreactors.

It is therefore the first object of the present invention a reduction process to obtain, stereoselectively, a compound of formula (I)

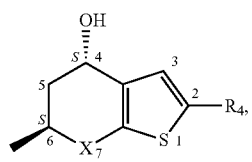

(I)

wherein X is S or $SO_2$ and $R_4$ is hydrogen or $SO_2NH_2$;

said process being characterised by asymmetric catalytic transfer hydrogenation of a compound of formula (II)

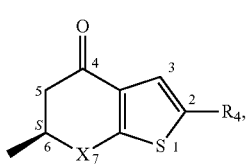

(II)

wherein X and $R_4$ are as defined above, using formic acid, a salt thereof, such as sodium, ammonium or triethylammonium formate (hereinafter also referred to as TEAF), or a $C_1$-$C_3$ alcohol as a hydrogen source, working in the presence of a base and of a catalyst of formula (III) or (IV)

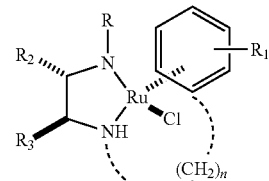

(III)

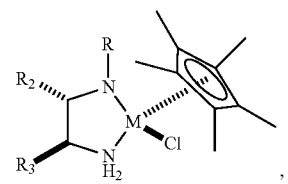

(IV)

wherein the dashed, curved line represents an optional single bond which exists when n is not zero; R is $SO_2C_6H_4$-p-$CH_3$ (hereinafter also referred to as Ts), $SO_2CH_3$ (hereinafter also referred to as Ms) or $SO_2C_6F_5$ (hereinafter also referred to as Fs); $R_1$ is absent, 1-$CH_3$-4-$CH(CH_3)_2$ (hereinafter also referred to as p-cymene), 1,3,5-$(CH_3)_3$ (hereinafter also referred to as mesitylene) or 1,3,4,5,6-$(CH_3)_6$ (hereinafter also referred to as hexamethylbenzene); $R_2$ and $R_3$ are both an unsubstituted phenyl group or $R_2$ and $R_3$, taken together, are a —$(CH_2)_4$— group; n is a number from zero to 3; and M is rhodium (Rh) or iridium (Ir).

According to the present invention, in a compound of formula (I), X is preferably $SO_2$.

According to the present invention, the hydrogen source is preferably formic acid or a salt thereof, such as sodium, ammonium or triethylammonium formate; in particular, the hydrogen source is formic acid.

According to the present invention with a $C_1$-$C_3$ alcohol it is meant methanol, ethanol, n-propanol and isopropanol, preferably isopropanol.

According to the present invention, the reduction takes place in the presence of a base, such as triethylamine; ammonia; an alkali hydroxide such as NaOH, KOH or LiOH; an alkaline earth hydroxide such as CaOH, MgOH or SrOH; sodium methylate; potassium methylate; sodium tert-butoxide or potassium tert-butoxide; the base is preferably triethylamine (hereinafter also referred to as TEA).

According to the present invention, when in a compound of formula (II) R4 is hydrogen, the reduction is preferably carried out in the presence of a catalyst of formula (III) in which n is zero, R is preferably Ts or Ms, in particular Ts; $R_1$ is preferably p-cymene or mesitylene, in particular p-cymene; and $R_2$ and $R_3$ are both an unsubstituted phenyl group. A catalyst of formula (III) in which n is zero, R is Ts, $R_1$ is p-cymene, and $R_2$ and $R_3$ are both an unsubstituted phenyl group, is particularly preferred and is also called RuCl(p-cymene)[(S,S)-Ts-DPEN].

According to the present invention, when in a catalyst of formula (III) n is 3, R is preferably Ts or Ms, in particular Ts; $R_1$ is absent; and $R_2$ and $R_3$ are both an unsubstituted phenyl group. A catalyst of formula (III) in which n is 3, R is Ts, $R_1$ is absent, and $R_2$ and $R_3$ are both an unsubstituted phenyl group is particularly preferred and is also called [(S,S)-teth-TsDpen-RuCl].

According to the present invention, a catalyst of formula (IV) in which M is rhodium (Rh), R is Ts, and $R_2$ and $R_3$, taken together, are a —$(CH_2)_4$— group, is particularly preferred and is also called Cp*RhCl[(S,S)-Tscydn].

According to the present invention, when in a compound of formula (II) $R_4$ is $SO_2NH_2$, the reduction is preferably carried out in the presence of a catalyst of formula (III) in which n is zero, R is Ts or Fs; $R_1$ is p-cymene; and $R_2$ and $R_3$ are both an unsubstituted phenyl group.

According to the present invention, the prefix trans- indicates the relative position of the substituents on the bicyclic structure of the compound of formula (I), and in particular indicates that the hydroxyl in position $C_4$ and the methyl in position $C_6$ are on two different sides of the same reference plane formed by said bicyclic structure.

Considering that a compound of formula (I) also has two chiral centers (one in position $C_4$ and the other in position $C_6$), the configuration of said chiral centers is such that the stereochemistry of the substituents of the compound of formula (I) obtained by means of the process of the present invention is 4S,6S.

According to the present invention, the term "stereoselectively" refers to the fact that the compound of formula (I) namely the compound trans-(4S,6S), is obtained with predominant yields compared to the undesired diastereoisomer cis-(4R,6S); preferably at least 90%, more preferably at least 95%, and even more preferably at least 99% of the product obtained is the diastereoisomer trans-(4S,6S).

A catalyst of formula (III), as defined above and in which n is equal to zero, can be prepared in situ by reacting a compound of formula (V)

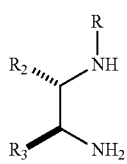

wherein R, $R_2$ and $R_3$ are as defined above, with a compound of formula (VI)

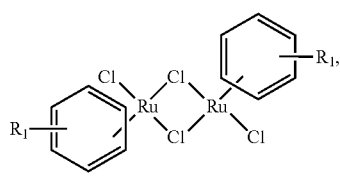

wherein $R_1$ is as defined above.

In a preferred aspect, in a compound of formula (V), R is preferably $SO_2C_6H_4$-p-$CH_3$ or $SO_2CH_3$; and $R_2$ and $R_3$ are both an unsubstituted phenyl group.

In another preferred aspect of the present invention, a compound of formula (V), wherein R is Ts or Fs, and $R_2$ and $R_3$ are both an unsubstituted phenyl group, also called (S,S)-TsDPEN or (S,S)-FsDPEN respectively, is reacted with a compound of formula (VI), wherein $R_1$ is p-cymene, also called (p-cymene) ruthenium dichloride dimer.

A catalyst of formula (IV), as defined above, can also be prepared in situ by reacting a compound of formula (V), as defined above, with a compound of formula (VII)

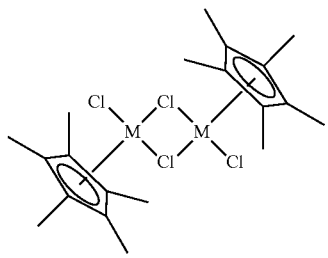

wherein M is rhodium (Rh) or iridium (Ir), preferably rhodium (Rh).

In a preferred aspect of the present invention, a catalyst of formula (III) or (IV) is preformed before contact with the reaction mixture; in particular, the catalyst RuCl(p-cymene)[(S,S)-Ts-DPEN] or the catalyst RuCl(p-cymene)[(S,S)-Fs-DPEN] is preformed before contact with the reaction mixture.

In another preferred aspect of the present invention, a cosolvent selected from a polar or an apolar aprotic solvent, including tetrahydrofuran (THF), acetonitrile (MeCN), ethyl acetate (EtOAc), isopropyl acetate (IPAC), dimethylformamide (DMF), dimethylacetamide (DMA), dichloromethane (DCM), N-methylpyrrolidone (NMP), methyl t-butyl ether (MTBE), or from alcohols is added to the reaction mixture; most preferably cosolvent is MeCN.

According to the present invention, the catalyst RuCl(p-cymene)[(S,S)-Ts-DPEN], which is formed before contact with the reaction mixture, is particularly preferred to obtain a compound of formula (I).

According to the present invention, the asymmetric reduction which allows to obtain stereoselectively a compound of formula (I) is carried out, for example, by stirring the ketone of formula (II) into a mixture of formic acid and TEA in the presence of the catalysts of formula (III) or (IV), and possibly in the presence of a cosolvent selected from THF, MeCN and EtOAc, preferably MeCN, at temperatures which can range from 0° C. to 100° C., preferably from 25° C. to 50° C., for periods of time selected appropriately by a person skilled in the art based on the amount and typology of the selected catalyst, based on the concentration of the substrate, and based on the relative amounts of formic acid and base, for example TEA.

In one aspect of the present invention, the asymmetric reduction which allows to obtain stereoselectively a compound of formula (I) is carried out, for example, by mixing a compound of formula (V) with a compound of formula (VI) or (VII) in the presence of formic acid and TEA, at a temperature ranging between 25° C. and 30° C., or as described in J. Am. Chem. Soc., 1995, 117, 7562-7563 or in J. Org. Chem., 1999, 64, 2186-2187, to give a catalyst of formula (III) or (IV) respectively. A ketone of formula (II) and possibly a cosolvent selected from THF, MeCN and EtAc, preferably MeCN, is added to the solution of the catalyst of formula (III) or (IV) prepared as indicated above, and the mixture is stirred at a temperature ranging between 28° C. and 30° C., for periods of time which can be established easily by a person skilled in the art depending on the quantity and typology of the catalyst, on the concentration of the substrate, and on the relative amounts of formic acid and TEA, to obtain the compound of formula (I).

According to the process of the present invention, the asymmetric reduction which allows to obtain, stereoselectively, a compound of formula (I) is also carried out by reacting the compound of formula (II) with a hydrogen source, such as sodium formate, formic acid or TEAF, in the presence of the catalysts of formula (III) or (IV), in a liquid/liquid (such as dichloromethane/water) or solid/liquid (such as heterogeneous catalyst in water) biphasic system, optionally in the presence of a phase transfer agent, and by reacting the mixture at a temperature ranging from 0° C. to 100° C., for periods of time which can be established easily by a person skilled in the art depending on the quantity and typology of the catalyst, and on the reaction medium.

A further object of the present invention is to prepare a compound of formula (I) in which X is $SO_2$ and $R_4$ is hydrogen by oxidation of a compound of formula (I) in which X is S and $R_4$ is hydrogen, as obtained above. Oxidation of a compound of formula (I) in which X is S and $R_4$ is hydrogen to give another compound of formula (I) in which X is $SO_2$ and $R_4$ is hydrogen is carried out by procedures known to a person skilled in that art; for example, as described in Blacklock et al., J. Org. Chem., 1993, 58 1672-1679 or in EP 2128161.

In a further aspect, the present invention includes a process for the preparation of dorzolamide, which includes preparation of a compound of formula (I) as described above, and conversion thereof into dorzolamide and optionally into the hydrochloride salt thereof.

A compound of formula (I) may be converted into dorzolamide by methods known in the art as described, for example, in Blacklock et al., J. Org. Chem., 1993, 58 1672-1679 or in EP 617037.

The starting compounds of formulae (II), (III), (IV), (V), (VI) and (VII) are commercially available and can be prepared by methods known in the art.

The present invention can be explained further by means of the examples below.

EXAMPLES

Example 1

Synthesis of 4H-thieno[2,3-b]thiopyran-4-ol,5,6-dihydro-6-methyl-,7,7-dioxide,(4S-trans); compound of formula (I) where $R_4$=H and X=$SO_2$ (p-cymene) ruthenium chloride dimer (17.8 mg, 0.03 mmol) and (S,S)-TsDPEN (25.4 mg, 0.07 mmol) were stirred in a formic acid:triethylamine mixture (3.69 g, molar ratio 5:2) under nitrogen at 28° C. for 20 minutes. The ketone (6S)-5,6-dihydro-6-methyl-4H-thieno[2,3-b]thiopyran-4-one 7,7-dioxide (1.0 g, 4.6 mmol, ee 92) was then added as a solid, and the mixture was left under stirring for 14 hours at 28° C. The reaction mixture was then filtered over silica and the panel was washed with ethyl acetate (50 mL). The filtrate was then washed with demineralised water (25.5 mL) and the aqueous phase was separated. The organic phase was washed with more demineralised water (24.6 mL) and the aqueous phase was separated. The reunited organic phases were then concentrated under vacuum and dried via azeotropic distillation with toluene to produce 4H-thieno[2,3-b]thiopyran-4-ol,5,6-dihydro-6-methyl-,7,7-dioxide,(4S-trans) as a mixture of trans:cis diastereoisomers equal to 92.6:7.4 (0.8 g, assay 93.1%, yield 74%, ee 99.8).

δH (400 MHz; $CDCl_3$) 7.6 (1H, d, Ar), 7.1 (1H, d, Ar), 4.9 (1H, m, C4-H), 3.8 (1H, m, C6-H), 2.6 (1H, m, C5-H), 2.4 (1H, m, C5-H), 2.1-1.9 (1H, b, OH), 1.5 (3H, d, C6-$CH_3$).

Example 2

Synthesis of 4H-thieno[2,3-b]thiopyran-4-ol,5,6-dihydro-6-methyl-,7,7-dioxide,(4S-trans); compound of formula (I) where $R_4$=H and X=$SO_2$ The complex RuCl(p-cymene)[(S,S)-Ts-DPEN] (5.9 mg, 0.009 mmol) was stirred into a formic acid:triethylamine mixture (2.33 g, molar ratio 5:2) under nitrogen at 28° C. The ketone (6S)-5,6-dihydro-6-methyl-4H-thieno[2,3-b]thiopyran-4-one 7,7-dioxide (1.0 g, 4.6 mmol, ee 98.7) was then added as a solid, and the mixture was left under stirring for two days at 28° C. Demineralised water (7.4 mL) was added to the mixture and the temperature was lowered to 20° C. After 1.5 hours at 20° C., the heterogeneous mixture was filtered and the precipitate was washed with demineralised water (1.8 g) to obtain 4H-thieno[2,3-b]thiopyran-4-ol,5,6-dihydro-6-methyl-,7,7-dioxide,(4S-trans)-(9CI) as a mixture of trans:cis diastereoisomers equal to 99:1 (0.5 g, assay 96.4%, ee 99.9).

$δ_H$ (400 MHz; $CDCl_3$) 7.6 (1H, d, Ar), 7.1 (1H, d, Ar), 4.9 (1H, m, C4-H), 3.8 (1H, m, C6-H), 2.6 (1H, m, C5-H), 2.4 (1H, m, C5-H), 2.1-1.9 (1H, b, OH), 1.5 (3H, d, C6-$CH_3$).

Example 3

Synthesis of 4H-thieno[2,3-b]thiopyran-4-ol,5,6-dihydro-6-methyl-,7,7-dioxide,(4S-trans) compound of formula (I) where $R_4$=H and X=$SO_2$ The catalyst RuCl(p-cymene)[(S,S)-Ts-DPEN] (0.49 g, 0.78 mmol) and acetonitrile (100.0 g) were added to a mixture of (6S)-5,6-dihydro-6-methyl-4H-thieno[2,3-b]thiopyran-4-one 7,7-dioxide (100.0 g, 96.5%, 446 mmol, 90.6 ee) in formic acid:triethylamine (100.0 g, molar ratio 5:2) under nitrogen at 28° C. After 18 hours of stirring and the addition of decolourising carbon (4.0 g), the mixture was stirred for one hour and then filtered. The filtered solution was added to demineralised water (600 mL) at 20° C. The mixture was then concentrated under vacuum, cooled to 10° C. and then the precipitate was filtered and washed with demineralised water (2×80 mL) to give 4H-thieno[2,3-b]thiopyran-4-ol,5,6-dihydro-6-methyl-,7,7-dioxide, (4S-trans)- as a mixture of trans:cis diastereoisomers equal to 99:1 (86.9 g, assay 96.9%, yield 86%, ee 99.9).

$δ_H$ (400 MHz; $CDCl_3$) 7.6 (1H, d, Ar), 7.1 (1H, d, Ar), 4.9 (1H, m, C4-H), 3.8 (1H, m, C6-H), 2.6 (1H, m, C5-H), 2.4 (1H, m, C5-H), 2.1-1.9 (1H, b, OH), 1.5 (3H, d, C6-$CH_3$).

Example 4

Synthesis of 4H-thieno[2,3-b]thiopyran-4-ol,5,6-dihydro-6-methyl-, (4S,6S); compound of formula (I) where $R_4$=H and X=S (p-cymene) ruthenium chloride dimer (16.6 mg, 0.03 mmol) and (S,S)-TsDPEN (19.9 mg, 0.05 mmol) were stirred into a formic acid/triethylamine mixture (4.7 g, molar ratio 5:2) under nitrogen at 28° C. for 20 minutes. The ketone (6S)-5,6-dihydro-6-methyl-4H-thieno[2,3-b]thiopyran-4-one (1.0 g, 5.4 mmol, ee 97) was then added as a solid, and the mixture was left under stirring for four days at 28° C. and for seven hours at 50° C. Demineralised water and IPAC were then added and the phases were separated. The aqueous phase was extracted twice with IPAC, and the reunited organic phases were washed with demineralised water. The organic phase (47.8 g) was concentrated under vacuum in a rotavapor, to obtain 4H-thieno[2,3-b]thiopyran-4-ol,5,6-dihydro-6-methyl-,(6S)— as a mixture of trans:cis diastereoisomers equal to 57.6:42.4 (0.98 g, GC assay 74.3%, yield 72%).

Example 5

Synthesis of (4S,6S)-4-hydroxy-6-methyl-5,6-dihydro-4H-thieno[2,3-b]thiopyran-2-sulfonamide; compound of formula (I) where $R_4=SO_2NH_2$ and $X=S$ A solution of catalyst RuCl(p-cymene)[(S,S)-Fs-DPEN] (27.4 mg, 0.0385 mmol) in TEAF (1.5 g, molar ratio 5:2) was added to a mixture of (6S)-5,6-dihydro-6-methyl-4H-thieno[2,3-b]thiopyran-4-one-2-sulfonamide (1.0 g, 3.80 mmol) in formic acid:triethylamine (2.16 g, molar ratio 5:2) under nitrogen at 28° C. After 16 hours, a solution composed of RuCl(p-cymene)[(S,S)-Fs-DPEN] (27.5 mg, 0.0386 mmol) in acetonitrile (1.2 g) was added to the mixture. After five days of stirring at 28° C., demineralised water (10.7 g) was added to the reagent mixture and the temperature was lowered to 10° C. The solid was filtered to obtain (6S)-4-hydroxy-6-methyl-5,6-dihydro-4H-thieno[2,3-b]thiopyran-2-sulfonamide as a mixture of trans:cis diastereoisomers equal to 61.7: 38.3 (0.32 g, yield 32%).

Example 6

Synthesis of 4H-thieno[2,3-b]thiopyran-2-sulfonamide,5,6-dihydro-4-hydroxy-6-methyl-,7,7-dioxide, (4S-trans)-; compound of formula (I) where $R_4=SO_2NH_2$ and $X=SO_2$ The catalyst RuCl(p-cymene)[(S,S)-Ts-DPEN] (22 mg, 0.0346 mmol) and acetonitrile (0.7 g) were added to a mixture of (6S)-4H-thieno[2,3-b]thiopyran-2-sulfonammide,5,6-dihydro-6-methyl-4-oxo-,7,7-dioxide (0.5 g, 1.69 mmol) in formic acid:triethylamine (1.06 g, molar ratio 5:2) under nitrogen at 28° C. Complete conversion into the reduction product was achieved after 4.5 hours. Demineralised water (2.67 g) and isopropyl acetate (8.7 g) were then added to the mixture and the phases were separated. The aqueous phase was extracted further with dichloromethane (10.7 g) and the phases were separated. The reunited organic phases were concentrated in a rotary evaporator under vacuum and dried via azeotropic distillation with toluene to provide 4H-thieno[2,3-b]thiopyran-2-sulfonamide,5,6-dihydro-4-hydroxy-6-methyl-,7,7-dioxide,(4S-trans)-(9CI) as a mixture of trans:cis diastereoisomers equal to 93:7 (0.41 g, yield 81%, ee 100).

4S-trans: δH (ppm) (400 MHz; DMSO) 8.0 (2H, bs, $SO_2NH_2$), 7.5 (1H, s, CH), 4.8 (1H, m, CH), 3.8 (1H, m, CH), 2.4 (1H, m, $CH_2$) 2.3 (1H, m, $CH_2$), 1.35 (3H, d, J=7 Hz, $CH_3$).

4S-cis: δH (ppm) (400 MHz, DMSO) 8.0 (2H, bs, $SO_2NH_2$), 7.5 (1H, s, CH), 6.1 (1H, bs, OH), 4.8 (1H, m, CH), 3.8 (1H, m, CH), 2.4 (1H, m, $CH_2$) 2.1 (1H, m, $CH_2$), 1.3 (3H, d, J=7 Hz, $CH_3$).

The invention claimed is:
1. A reduction process to obtain, stereoselectively, a compound of formula (I)

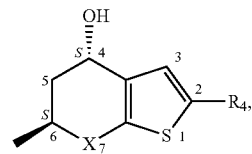

wherein X is S or $SO_2$ and $R_4$ is hydrogen or $SO_2NH_2$;
said process comprising asymmetric catalytic hydrogenating by hydrogen transfer a compound of formula (II),

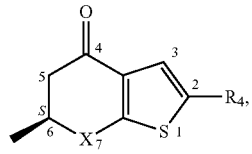

wherein X and $R_4$ areas defined above, using formic acid, a salt thereof, said salt being sodium, ammonium or triethylammonium formate, or a $C_1$-$C_3$ alcohol as a hydrogen source, working in the presence of a base and of a catalyst of formula (III) or (IV),

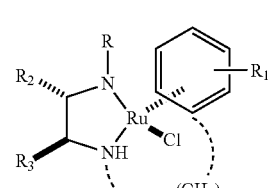

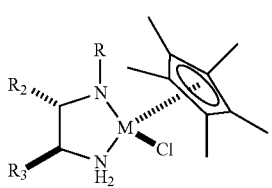

wherein the dashed, curved line represents an optional single bond which exists when n is not zero; R is $SO_2C_6H_4$-p-$CH_3$, $SO_2CH_3$ or $SO_2C_6F_5$; $R_1$ is absent, 1-$CH_3$-4-$CH(CH_3)_2$, 1,3,5-$(CH_3)_3$ or 1,3,4,5,6-$(CH_3)_6$; $R_2$ and $R_3$ are both an unsubstituted phenyl group or $R_2$ and $R_3$, taken together, are a —$(CH_2)_4$— group; n is a number from zero to 3; and M is rhodium (Rh) or iridium (Ir) and wherein the compound of formula (I), is obtained with a yield of at least 90% compared to the diastereoisomer cis-(4R,6S).

2. The process according to claim 1, wherein X is $SO_2$.
3. The process according to claim 1, wherein the hydrogen source is formic acid or a salt thereof, said salt being sodium, ammonium or triethylammonium formate.
4. The process according to claim 1, wherein the hydrogenating step takes place in the presence of a base selected from triethylamine, ammonia; an alkali hydroxide, an alkaline earth hydroxide, methylated sodium, methylated potassium, sodium tert-butoxide and potassium tert-butoxide.

5. The process according to claim 4, wherein the base is triethylamine.

6. The process according to claim 5, wherein a cosolvent is acetonitrile.

7. The process according to claim 1, wherein the hydrogenating step takes place in the presence of a catalyst of formula (III).

8. The process according to claim 1, wherein the reduction takes place in the presence of a catalyst of formula (IV).

9. The process according to claim 1, wherein a catalyst of formula (III), wherein n is equal to zero, is prepared in situ by reacting a compound of formula (V)

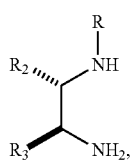
(V)

wherein R is $SO_2C_6H_4$-p-$CH_3$, $SO_2CH_3$ or $SO_2C_6F_5$, $R_2$ and $R_3$ are both an unsubstituted phenyl group or $R_2$ and $R_3$, taken together, are a —$(CH_2)_4$— group, with a compound of formula (VI)

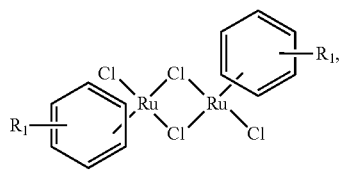
(VI)

wherein $R_1$ is absent, 1-$CH_3$-4-$CH(CH_3)_2$, 1,3,5-$(CH_3)_3$ or 1,3,4,5,6-$(CH_3)_6$.

10. The process according to claim 9, wherein, in a compound of formula (V), R is $SO_2C_6H_4$-p-$CH_3$, and $R_2$ and $R_3$ are both an unsubstituted phenyl group.

11. The process according to claim 10, wherein, in a compound of formula (VI), $R_1$ is 1-$CH_3$-4-$CH(CH_3)_2$.

12. The process according to claim 1, wherein a catalyst of formula (IV is prepared in situ by reacting a compound of formula (V)

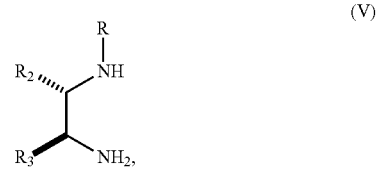
(V)

wherein R, $R_2$ and $R_3$ are as defined in claim 1, with a compound of formula (VII)

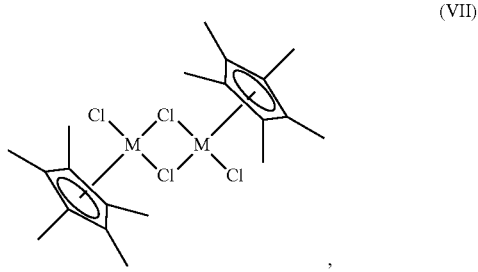
(VII)

wherein M is rhodium (Rh) or iridium (Ir).

13. The process according to claim 1, wherein the catalyst of formula (III) or (IV) is formed before contact with the reaction mixture.

14. The process according to claim 13, wherein the catalyst is RuCl(p-cymene)[(S,S)-Ts-DPEN].

15. The process according to claim 1, further comprising the transformation of the compound of formula (I) into dorzolamide or into the hydrochloride salt thereof.

* * * * *